(12) United States Patent
Weatherhead

(10) Patent No.: US 8,602,791 B2
(45) Date of Patent: Dec. 10, 2013

(54) GENERATION OF TEST STIMULI IN VISUAL MEDIA

(75) Inventor: James J. Weatherhead, San Diego, CA (US)

(73) Assignee: Eye Tracking, Inc., San Diego, CA (US)

( * ) Notice: Subject to any disclaimer, the term of this patent is extended or adjusted under 35 U.S.C. 154(b) by 1574 days.

(21) Appl. No.: 11/594,041

(22) Filed: Nov. 6, 2006

(65) Prior Publication Data

US 2007/0105071 A1    May 10, 2007

Related U.S. Application Data

(60) Provisional application No. 60/733,676, filed on Nov. 4, 2005.

(51) Int. Cl.
G09B 19/00    (2006.01)

(52) U.S. Cl.
USPC .......................................... 434/236; 434/322

(58) Field of Classification Search
USPC ............. 434/322, 323, 236; 351/209; 396/51; 715/863; 345/660
See application file for complete search history.

(56) References Cited

U.S. PATENT DOCUMENTS

| | | | |
|---|---|---|---|
| 3,691,652 A | | 9/1972 | Clynes |
| 4,012,128 A | | 3/1977 | Regan |
| 4,789,235 A | * | 12/1988 | Borah et al. ................. 351/246 |
| 4,931,865 A | | 6/1990 | Scarampi |
| 5,243,517 A | * | 9/1993 | Schmidt et al. ............... 600/544 |
| 5,280,793 A | | 1/1994 | Rosenfeld |
| 5,331,969 A | | 7/1994 | Silberstein |
| 5,410,376 A | * | 4/1995 | Cornsweet et al. ........... 351/210 |
| 5,564,433 A | | 10/1996 | Thornton |
| 5,617,872 A | | 4/1997 | Scinto et al. |
| 5,620,436 A | | 4/1997 | Lang et al. |
| 5,632,282 A | | 5/1997 | Hay et al. |
| 5,649,061 A | | 7/1997 | Smyth |
| 5,651,107 A | | 7/1997 | Frank et al. |
| 5,704,369 A | | 1/1998 | Scinto et al. |
| 5,724,987 A | | 3/1998 | Gevins et al. |

(Continued)

FOREIGN PATENT DOCUMENTS

| AU | 5865600 A | 10/2000 |
|---|---|---|
| EP | 1164919 A1 | 1/2002 |

(Continued)

OTHER PUBLICATIONS

"A Gaze-Responsive Self-Disclosing Display"; Starker et al.; CHI '90 Proceedings, Media Lab, Massachusetts Institute of Technology (Apr. 1990).

(Continued)

*Primary Examiner* — Peter Egloff
(74) *Attorney, Agent, or Firm* — Mintz Levin Cohn Ferris Glovsky and Popeo, P.C.

(57) ABSTRACT

Test stimuli for visual media may be generated by incorporation of one or more element images selected from a library into a presentation area. The test stimuli may be displayed or presented to one or more subjects and metrics indicating the attentiveness of the subjects to various locations in the composite image may be measured. These metrics may be analyzed with placement parameters for incorporation of the element images into the composite image to determine subject reactions to various aspects of the test stimuli.

30 Claims, 4 Drawing Sheets

(56) References Cited

U.S. PATENT DOCUMENTS

| | | | |
|---|---|---|---|
| 5,751,283 A * | 5/1998 | Smith | 715/798 |
| 5,886,683 A | 3/1999 | Tognazzini et al. | |
| 5,963,300 A | 10/1999 | Horwitz | |
| 5,982,555 A | 11/1999 | Melville et al. | |
| 6,024,707 A | 2/2000 | Scinto et al. | |
| 6,067,565 A | 5/2000 | Horvitz | |
| 6,070,098 A | 5/2000 | Moore-Ede et al. | |
| 6,090,051 A | 7/2000 | Marshall | |
| 6,102,846 A | 8/2000 | Patton et al. | |
| 6,102,870 A | 8/2000 | Edwards | |
| 6,106,119 A | 8/2000 | Edwards | |
| 6,422,870 B1 * | 7/2002 | Ohsawa | 434/236 |
| 6,437,758 B1 * | 8/2002 | Nielsen et al. | 345/8 |
| 6,507,802 B1 | 1/2003 | Payton et al. | |
| 6,572,562 B2 | 6/2003 | Marshall | |
| 6,601,021 B2 * | 7/2003 | Card et al. | 702/187 |
| 6,608,615 B1 | 8/2003 | Martins | |
| 6,694,486 B2 * | 2/2004 | Frank et al. | 715/203 |
| 6,712,468 B1 | 3/2004 | Edwards | |
| 6,728,752 B1 | 4/2004 | Chen et al. | |
| 6,896,655 B2 | 5/2005 | Patton et al. | |
| 7,029,121 B2 | 4/2006 | Edwards | |
| 7,120,880 B1 * | 10/2006 | Dryer et al. | 715/863 |
| 7,284,201 B2 * | 10/2007 | Cohen-Solal | 715/738 |
| 7,711,208 B2 * | 5/2010 | Grunder | 382/298 |
| 2001/0011211 A1 | 8/2001 | Bushey et al. | |
| 2002/0015064 A1 | 2/2002 | Robotham et al. | |
| 2002/0107972 A1 | 8/2002 | Keane | |
| 2003/0038754 A1 | 2/2003 | Goldstein et al. | |
| 2003/0069616 A1 | 4/2003 | Skene et al. | |
| 2003/0078513 A1 | 4/2003 | Marshall | |
| 2003/0225591 A1 | 12/2003 | Clay et al. | |
| 2004/0075645 A1 | 4/2004 | Taylor et al. | |
| 2007/0050253 A1 * | 3/2007 | Biggs et al. | 705/14 |

FOREIGN PATENT DOCUMENTS

| | | |
|---|---|---|
| WO | WO99/18842 | 4/1999 |
| WO | WO00/54654 | 9/2000 |
| WO | WO01/74236 | 10/2001 |
| WO | WO03/092482 | 11/2003 |
| WO | WO/2004/084117 | 9/2004 |

OTHER PUBLICATIONS

"Development of Predictive Chi with Eye Movements"; Takagi, H.; Master Thesis, University of Tokyo (Feb. 7, 1996).

"The Index of Cognitive Activity: Measuring Cognitive Workload"; Sandra P. Marshall; In Proceedings of the 2002 IEEE 7th Conference on Human Factors and Power Plants; New York: IEEE; .7.5-7.10.

"Integrating Psychophysiological Measures of Cognitive Workload and Eye Movements to Detect Strategy Shifts"; Marshall et al.; Proceedings of the 36th Annual Hawaii International Conference on Systems Sciences, Los Alamitos, CA: IEEE; Jan. 2003 (6 pages).

eyetools™ home page; http://www.eyetools.com; printed Feb. 21, 2006.

Ahern and Beatty, Science (1979) 205:1289-1292.

Bradshaw, Quarterly Journal of Experimental Psychology (1968) 20:116-122.

Davidson and Sutton, Current Opinion in Neurobiology (1995) 5:217-224.

Gardner et al., Perceptual and Motor Skills (1975) 41:951-955.

Granholm et al., Psychophysiology (1996) 33:457-461.

Hess and Polt, Science (1964) 140:1190-1192.

Kim et al., Cortex (1998) 34:753-762.

Lowenfeld, in The Pupil: Anatomy, Physiology and Clinical Applications, vol. I; Ames, Iowa, Iowa State University (1993) pp. 83-89.

Metalis et al., Journal of Applied Psychology (1980) 65:359-363.

Schluroff, Brain and Language (1982) 17:133-145.

Wierwille et al., "Research on vehicle-based driver status/performance monitoring: development, validation, and refinement of algorithms for detection of driver drowsiness" National Highway Traffic Safety Administration Final Report: DOT HS 808 247, VPISU Report No. 94-04, Dec. 1994.

Wierwille, et al., "Research on Vehicle-Based Driver Status/Performance Monitoring, Part III", USDOT HS 808 640, Sep. 1996.

Tijerina, et al., "A Preliminary Assessment of Algorithms for Drowsy and Inattentive Driver Detection on the Road", USDOT HS 808 (TDB) Mar. 1999.

* cited by examiner

GENERATION OF TEST STIMULI IN VISUAL MEDIA

RELATED APPLICATIONS

This application claims the benefit of priority from U.S. Provisional Application entitled "GENERATION OF TEST STIMULI IN IMAGES", filed Nov. 4, 2005, Application Ser. No. 60/733,676, the disclosure of which is incorporated by reference in its entirety.

TECHNICAL FIELD

The subject matter described herein relates to the generation and arrangement of test stimuli in visual media.

BACKGROUND

Eye tracking is a technique used to determine where a person is looking. In brief, the movements of a subject's eyes are tracked while the subject is presented with various visual media. Further information may also be gleaned from observing and quantifying other movements and changes in the pupils as the subject observes specific sub-aspects of a visual stimulus.

Test stimuli are images or other media that may be presented to test subjects for the purposes of gauging subject interest in one or more aspects of a stimulus. Various techniques exist for identifying a specific region or regions of a given test stimulus that attract attention from a subject viewing it. Advertisers, web page designers, and other creators of marketable content may use test stimuli with one or more test subjects to improve visibility of a desired brand or product placement, or to test the impacts of different media layouts on the emotional response of those viewing them.

SUMMARY

In a first aspect, a composite image is generated that includes an element image selected from a library. The element image is located within the composite according to one or more placement parameters which are tracked. The composite image is presented to a subject, and a metric indicative of user attentiveness to one or more locations in the composite image is recorded. The recorded metric is correlated with the one or more placement parameters to characterize a level of subject interest in the element image.

Optionally, in further interrelated aspects, the placement parameters may be stochastically generated and/or the element image may be stochastically selected from either all of the element images in the library or from a user-defined subset of element images in the library. The stochastically obtained placement parameters may be selected from one or more of a location within the composite image, an absolute dimension of the element image, a relative dimension of the element image, an orientation of the element image, a metric of a degree to which the element image is occluded by one or more features of the composite image, and a metric of transparency of the element image or a part thereof.

The library may also optionally be defined by selection of one or more selected element images. A plurality of regions may optionally be defined within the composite image such that the element image may be placed into one of the plurality of regions. The metric of subject attentiveness may optionally be eye tracking data or input from a user input device. Additionally, an additional element image may be selected from the library and included in one or more of the composite images in the sequence of composite images. The composite image may also optionally be presented to the subject as one of a sequence of test stimuli.

In a second aspect, an element image selected from a library is scaled relative to a content of a presentation area. The element image is incorporated into the presentation area at a defined location to form a composite image, and information related to the incorporation of the element image into the composite image is recorded. The composite image is presented to one or more test subjects and external data related to the test subject viewing of the composite image are recorded. The external data are analyzed in correlation with the information related to incorporation of the element image in the composite image to characterize a level of subject interest in the element image.

In further optional aspects, the defined location may be determined stochastically. The external data may optionally be eye tracking data or input from a user input device that are related to one or more locations within the composite image. The information related to incorporation of the element image in the composite image may optionally be a location of the element image within the composite image, a dimension of the element image within the composite image, an orientation of the element image within the composite image, a staging of the element image within the composite image, and the like. The analysis may optionally include correlating a frequency with which the external data intersect an area occupied by the element image in the composite image, correlating a frequency with which the external data transfer into or out of an area occupied by the element image in the composite image, correlating a sequence in which the external data transition between an area occupied by the element image in the composite image and another area within the composite image, and the like.

In further optional aspects, second external data may be recorded at a time corresponding to an instance in which the external data intersect an area occupied by the element image in the composite image, at a time corresponding to an instance in which the external data transfer into or out of an area occupied by the element image in the composite image, and/or at a time corresponding to an instance in which the external data transition between an area occupied by the element image in the composite image and another area within the composite image. The second external data may be produced from one or more sources selected from computer input devices and psycho-physiological measuring devices. The scaling may optionally be performed using a scaling algorithm.

In a third aspect, a plurality of composite images is presented to a plurality of subjects. Each composite image is generated by incorporating one or more of a plurality of element images selected from a library into a presentation area according to one or more placement parameters. A metric indicative of attentiveness of each of the plurality of subjects to one or more locations in the plurality of composite images is recorded, and the recorded metric is correlated with the one or more placement parameters to characterize a level of subject interest in the element image.

In optional interrelated aspects, the one or more element images incorporated into each composite image in the plurality of composite images may be selected stochastically from the library. In another optional aspect, the one or more placement parameters for each of the one or more element images in each of the plurality of composite image may be stochastically generated. A different ordering in which the plurality of composite images is shown to one or more of the plurality of subjects may also be stochastically generating. The records of the metric indicative of subject attentiveness may also be aggregated and analyzed by one or more statistical measures.

In further aspects, an article may include a machine-readable medium that stores instructions operable to cause one or more machines to perform one or more of the operations described above. A computing device may optionally include a machine readable medium the stores these instructions. This computing device may operate to perform one or more of the operations described above.

DESCRIPTION OF THE DRAWINGS

1. This disclosure may be better understood upon reading the detailed description and by reference to the attached drawings, in which.

DETAILED DESCRIPTION

Figure 1:
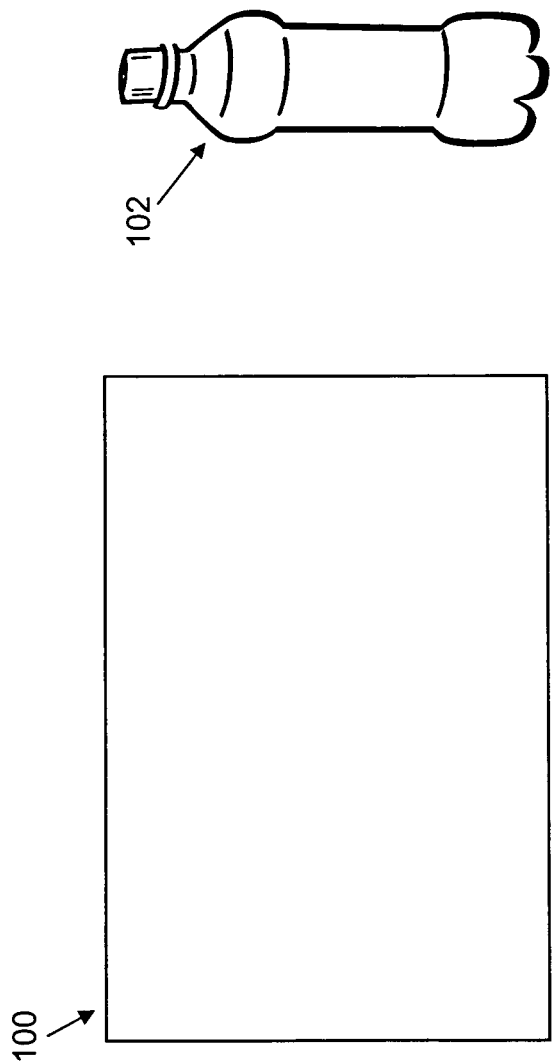
FIG. 1 is a diagram illustrating an example of incorporation of an element image in a composite image.

Quantification of the level of attention paid to and the emotional response evoked by various aspects of visual media presented to one or more viewers is of increasing interest in a variety of fields. The present disclosure addresses methods, techniques, systems and articles for rapidly building visual stimuli from a library of images. While the following description of the disclosed subject matter addresses various aspects that may be of use in research studies, it will be readily appreciated that the underlying technique may be utilized for other applications. The descriptions of various applications of the subject matter are intended to be illustrative, not limiting. Various features of the disclosed subject matter facilitate randomization of composite image construction and recordation of the locations of various elements placed in the composite image and may simplify research utilizing eye-tracking and similar methodologies.

In general, the disclosed subject matter deals with the construction of one or more composite images from elements contained in a library. This library is predefined with various element images or other potential image elements. The library may include one or more entries or elements. Each element generally includes an element image (such as for example a digital image file such as a bitmap), one or more dimensioning values, and some unique identifier that can be used to reference the element. Image elements may also include information describing one or more image sub-elements within a given image element. For example, an image element that includes an image of a bottle might also include information about the location of a label on the bottle.

The dimensioning values ma y include either defined or arbitrary units. The dimensioning value need not relate to the object depicted in the element image. However, the dimensioning value will generally correspond to the physical dimensions of an object to which the image relates. For example, if an element image is of a side profile of a box, the dimensioning values associated with the element image could be the physical measurements of the pictured box. This information may be used to scale element images appropriately for incorporation into a composite picture.

An element image may optionally be a subimage, for example a portion of a larger picture, or a subsection of an image. In this case, the entry may include information that defines that portion of the larger image, such as a series of points that define that portion, or some mathematical function that defines that portion. Defined subimage areas may optionally be regular or irregular shapes.

Element images in the disclosed subject matter may also be video clips. Alternatively, one or more elements from a video clip may be included in the library. If the element image is sourced from a video file, then the location of the video file or stream may be associated with the element image in the library. Additional information such as for example a frame identifier, such as for example a frame index, media time, or the like, may also be associated to indicate at what point in the video stream the image is taken. Portions of a video sourced image may also be defined by additionally providing region information as mentioned for static image entries.

A library may contain any number of element images. In one implementation, one or more rules or techniques may be applied to facilitate management of the elements. For example, one or more attributes may be attached to an element. A user may then query the library for all images that have an attribute or attributes matching the constraints of the given query. Alternatively, one or more categories may be defined, and elements may be associated with one or more of these categories. A library query for a given category would return all elements associated with that category. For example, an element image of a beverage or a beverage container could be associated with a category called "drinks." Attributes and categories may be textual, such as for example a descriptive word or phrase, graphical, such as for example a pattern or image that is descriptive or representative of the element image.

The subject matter described herein may build composite images either manually, such as for example with explicit user input as to the selection of element images, their placement or the like, or automatically, such as for example through the action of a computer program that implements one or more aspects of the process of constructing one or more composite images. In general, one or more element images are placed into a presentation area to form a composite image. A presentation area may be a blank screen area, a colored background, an image that already contains one or more other images or element images from the library or another library, or the like. For either the manual or automatic mode, a number of settings may be adjusted. These include, but are not limited to, one or more background colors of the presentation area image or the element image, size of the element image (for example in terms of pixels or some other definition of display size), a background image or images or lack thereof that are placed in the background of the composite image behind one or more element images added to the composite image, a foreground image or images or lack thereof that are placed in the foreground of the presentation area that may or may not partially obscure one or more of the element images added to the composite image, and one or more or zero colors that are to be regarded as transparent during the compilation process (this may apply to all element images or specific element images or to background or foreground image in the presentation area).

In some implementations, a setting may be included that allows the physical size of an image element or what it represents to be deduced. As an illustrative example, user or automated inputs to the composite image construction process may include information such as "the width of this image equates to 2000 millimeters" and "the presentation area is physically 100 millimeters wide." Designating one or more physical dimensions of the composite image and/or library element images allows for accurate scaling of the images brought into the composite image from the library. Dimension values given for an element in the library may be used to scale the visual representation of the element image to the physical dimensions of the composite image.

Figure 2:
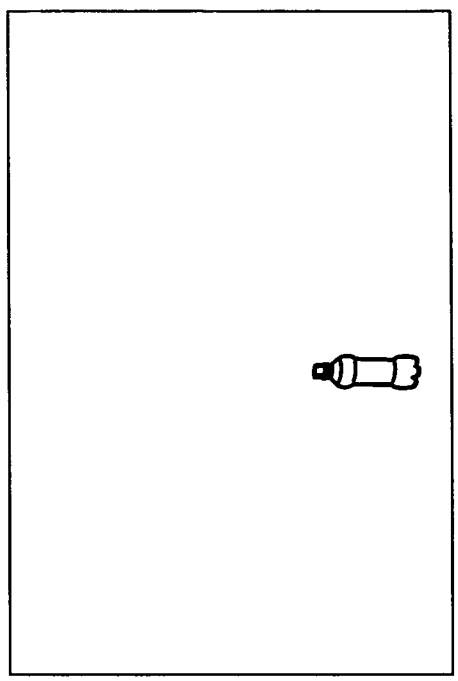
FIG. 2 is a diagram illustrating an example of a composite image incorporating an element image.

This principal is illustrated in the example diagrams shown in FIG. 1 and FIG. 2. FIG. 1 shows a defined presentation area 100. This is the size of the composite image that will be output when it is completed). In this example, the resolution is set to 1024×768 pixels, but the physical dimensions that will be used to scale element images inserted from the image library is set to 200×400 cm (width×height). The ratio between physical dimensions and actual dimensions need not match. Next, an element image 102 from the library is selected for insertion into the presentation area to form the composite image. The resolution of this element image is 200×768 pixels, which in this example is comparable to that of the composite image. However, the physical dimension of the object pictured in the element image is much smaller than that of the scene depicted in the composite image. For example, the image element 102 shown in FIG. 1 is a soft drink bottle whose physical dimensions are 8×20 cm. When the element image is inserted into the presentation area, the element image is rescaled using the physical dimensions of both the element image and the composite image to yield the completed composite image 200 shown in FIG. 2.

In this example, a linear equation may be used to achieve the rescaling effect. Alternatively, nonlinear scaling equations may also be used. In the example of a linear scaling, the ratio of the element image to the composite image using physical dimensions is as follows: the width ratio=8 cm/200 cm=0.04, and the height ratio=20 cm/400 cm=0.05. Therefore, in this example the element image size is resized to that ratio of composite image as follows: width=1024 pixels× 0.0.4=40.96 pixels and height=768 pixels×0.05=38.4 pixels such that the approximate scaled size of the element image in the completed composite image is approximately 41×38 pixels.

The act of scaling an image (bigger or smaller) may have a substantial effect on the quality of the image. As an illustrative example, shrinking an image from its original dimensions of 2000×1000 pixels) to a new size of 1000×500 may be accomplished by first creating a new temporary image of size 1000×1000 into which every other column from the original image is copied. Then, the final, destination image is created by copying every other row from the temporary 1000×1000 image into the final 1000×500 pixel image. While this method is effective in shrinking the image, it may result in a poor quality scaled image. The amount of degradation depends on numerous factors including the composition in the original image, how much the image was shrunk, and the like. The underlying cause for the degradation is the arbitrary chopping of pixels from the original image, the remaining pixels were used.

One way to reduce degradation in image quality when scaling is use a resizing algorithm, one or more of which may be incorporated into the disclosed subject matter. Various algorithms may be used, including but not limited to Lanczos 3, Hanning, and the like. While each such algorithm is different, their operative principles are typically similar. Whether upsizing or shrinking an image, these algorithms generally use other pixels in the original image to estimate a "most appropriate" pixel to place into the scaled image. An example of how such a resizing algorithm might operate may be illustrated using the hypothetical 2000×1000 pixel image discussed above. To rescale the image to 1000×500 pixels, a scaling algorithm might first create a new blank destination image of 1000×500 pixels, then traverse the new image pixel by pixel, calculating the current offset into the target image, then using that to identify the corresponding pixel in the original image (based on ratio), then averaging the values of a defined number of pixels in the locale of that point in the original image to identify the value for the pixel in the destination image.

In some implementations, one or more regions or locations may be defined on the presentation area into which element images may be placed. These regions or locations may be defined by a variety of techniques. For example, one or more specific points may be explicitly designated. Alternatively a region comprising a series of points or a mathematical function that defines an area may be defined. Each location may be identified via some unique identifier. An additional example of identifying a valid region is to define one or more "shelves" such as for example horizontal rows or vertical columns in the composite image area. In this example, library images may be placed anywhere on a row or in a column, or at defined areas within a row or a column. The designation of regions and locations on the composite image is not constrained by Cartesian coordinate systems, either. A radial or Euclidian (relative) geometric system may also be defined to designate and record the locations of element images placed in the composite image.

In one implementation, composite images may be built manually by selecting one or more element images from the library and placing them onto valid locations or regions within the composite image area. As element images are brought into the presentation area, they are scaled to be in proportion with the final composite image and its background and foreground image (as discussed previously). In automatic mode, one or more predefined instruction(s) or method(s) may be followed to generate one or more composite images. The element images used in each composite image may be randomly or stochastically selected from entries in the library. Throughout this disclosure, "stochastic" refers to both fully randomized selection and to pseudo-randomizations performed using one or more statistical algorithms. Statistical design methods, such as for example Latin Square and Greco-Latin Square methods may also be utilized. Alternatively, element images may be randomly or stochastically selected from one or more subsets of element images in the library, or they may be explicitly specified by the user. As an example, a user may designate that composite image 1 contains element image 1 and element image 3, and that composite image 2 contains element image 5 and element image 6.

Similarly, the locations at which the element image or images are placed within the presentation area may be randomized, explicitly stated for each composite image, or randomized within some subset of locations or regions within a composite image. As an example of randomizing element images within a subset of locations or regions, composite image 1 may be designated as including element image 3 placed within any of locations A, F or G. A location would randomly be chosen for that element image from the designated locations. A requirement that two image elements not occupy the same location within a composite image may also be included.

Many randomization algorithms exist, any of which could be incorporated to facilitate generation of composite images with desired randomization of element image selection and/or location and sizing. Examples of algorithms that may be used in conjunction with the subject matter disclosed herein are the Latin Square and the Greco-n Latin Square randomization methods. Other algorithms that operate similarly or that give similar results, including randomization functions available through computer programming languages, may also be used.

Similar visual scaling effects to those mentioned above may be achieved by building a three-dimensional (3-D) scene using the library dimensions. In such an implementation, the final rendered scene may be captured as the composite image. For example, a composite image may be generated by first generating a 3-D scene from one or more element images whose image attributes include a digital rendering of a 3-D shape. In this manner, the element image may be placed in the composite image in one or more orientations. Once the 3-D scene is rendered, it may be captured to a two dimensional image for use as described above. The ability to record where each element image is placed in the final two dimensional composite image readily supports correlation of various aspects of the composite image or images with external data as discussed in greater detail below.

For each element image incorporated into a composite image, a record may be kept of positional information, such as for example location within the composite image (either deterministic or within a predefined regional area of the composite image), orientation, scaling or dimensions of the element image within the composite image, transparency, and placement in the foreground or background of the composite image. This information may be calculated from many different pieces information. The exact description of the information is not needed provided that information allows various aspects of the relationship of the element image to the composite image as a whole to be recorded.

Recordation of the above information about element image relationships to the composite image, and by deduction or other means, to other element images within the composite image may facilitate a number of data processing and correlation techniques. These techniques may include aggregation of data regarding placement of the images and correlations of "external data" against these data for positional and other data regarding characteristics of the element images within the composite image. Examples of external data include, but are not limited to: eye-tracking data, input from user input devices such as a mouse or a stylus, or any other information that can be associated with a position or region on the composite image. These examples may include measurements with resolutions as fine as a pixel location that was seen, to those as crude as whether a mouse cursor was clicked on a particular region within the picture and if so, how many times this occurred. Eye tracking data may include one or more of gaze direction or a location on a screen where a subject's attention is focused, pupil movements and dilation, eyelid separation, gaze direction when blinks occur, blink duration and frequency, divergence of right and left eye gaze directions, and saccade or fixation of a subject's gaze.

Various analyses may be performed using external data in relation to the recorded characteristics of element images incorporated into a composite image or sequence of composite images that are presented to one or more test subjects. Illustrative and non-limiting examples of these analyses include recording the number of times external data intersect with (falls within or optionally, touches the boundary) of a given region, counting the number of times external data transfer into and then out of a given region, and calculating the order in which external data transition from one region to the other. In addition, one or more other data sources may be interrogated such that a value of such data is recorded at the time a region is intersected, or on the first intersection of the external data and a given region, or some similar event. Examples of other data sources include, but are not limited to: computer input devices, and psycho-physiological measures including such metrics as cognitive workload, cognitive activity, cognitive engagement, measures of affective response, cognitive state, blink information, saccade and fixation information. Source of these data similarly may be derived from any means including but not limited to: EEG, fMRI, EKG, fNIR, ECG, Galvanic Skin Response, and Pupillometry.

These computations may be made for a single person viewing the test stimuli, or aggregated across groups of people that may match one or more defined demographic categories. As an example, responses may be aggregated across all male or all female respondents. Alternatively, age or income level may be used. Any means of categorizing and analyzing the collected data are within the scope of this disclosure. Similarly, results may be compared across groups of people, or individual results may be compared to those of any other combinations of groups. Not all subjects in a test group need to see all of the composite images prepared in a sequence.

Results generated by the disclosed subject matter may be textual, graphical, or other representations of the data. Graphical representations may include alterations of the composite image or images that a respondent or group of test subject respondents saw. For example, alterations to the composite image or images may include coloring changes that depict levels of data, or changing alpha levels within the picture (or overlay) to depict levels of data, or some combination of both.

The disclosed subject matter may support both transparent images and transparent colors. For example, it could be specified that the color blue is transparent for all element images placed within any given composite image. This effect may be to make all element images, background images and foreground images transparent where they were originally colored, for example, blue. As such, images placed behind those blue areas will become visible. This technique is known as alpha blending.

An illustrative example of this technique may be applied to create a composite image of a shelf in a supermarket or other retail outlet. The element images to be included may be frozen food products, and a foreground image to be included in the composite image may be a glass freezer door. The desired effect could be to create an image as though the viewer is looking at one or more element images through a glass freezer door. This effect may be achieved if for example the outer frame of the door is portrayed in a metallic or other realistic color while the glass piece of the door image is set to some other unused color, such as for example green. The color green may be set to be a transparent color in the composite image. Then, the element images of products to be placed within the frozen food display may be placed in the scene before the freezer door image element is placed in the foreground. The element images of the products will be visible through the glass area of the door as the green area of the door will become transparent.

Different alpha levels may be set for the alpha blending process. This technique has the effect of making an object appear transparent, semi-transparent or opaque. Images in the library may store transparency information within the bitmap definition itself, or within the library entry for that element image. In this manner, transparent colors need not be specified. Rather, transparency information may be set on the element image itself. In this case, transparency would be applied only to the element image in question.

If for any reason alpha blending is not appropriate for any implementation of the disclosed subject matter, a similar effect may be achieved by reading only visible pixels from the element image and editing the composite image directly. For example, the invisible pixels are not read and thus not applied to the composite image.

Figure 3:
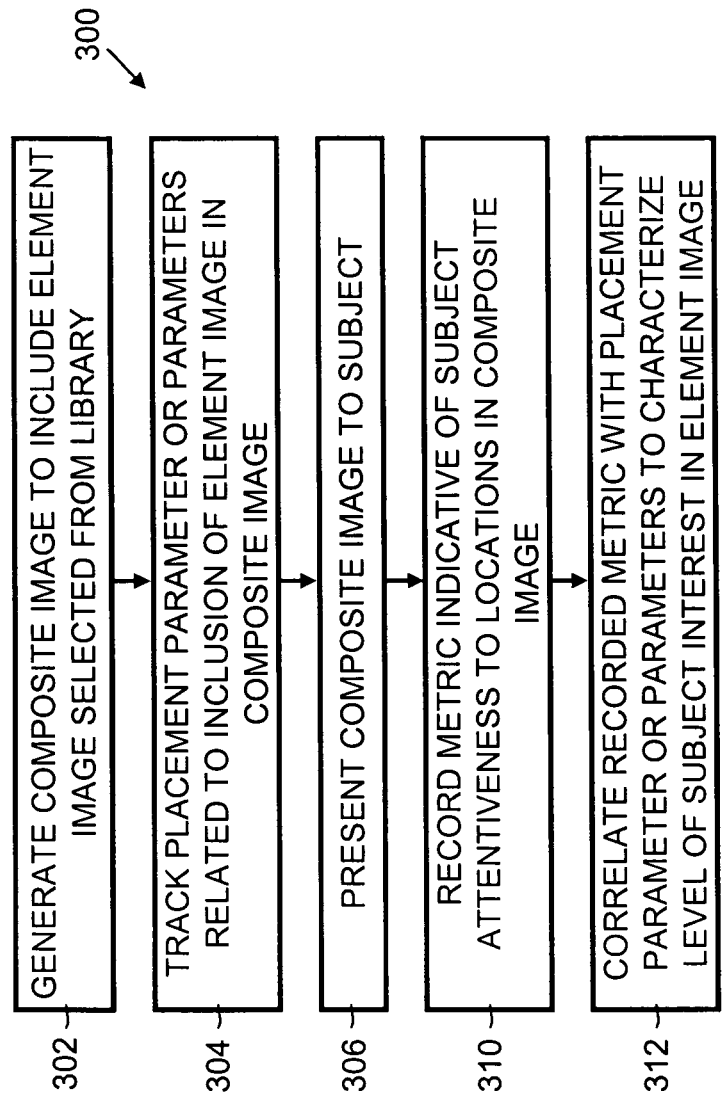
FIG. 3 is a flow chart diagram illustrating a first example of a method of constructing a composite image containing test stimuli.

FIG. 3 presents a method flow diagram 300 illustrating an example of one example implementation of the disclosed subject matter. In general, an element, such as for example an element image, may be selected from a library for testing. A composite image is generated to include the element image 302. One or more placement parameters related to inclusion of the element image in the composite image are tracked 304. Examples of placement parameters include but are not limited to coordinates related to the placement of the image element in the presentation area, a pre-defined region where the image element is placed, dimensions of the image (either absolute or relative to the composite image dimensions), whether the element image is in the presentation area foreground or in the background and/or occluded by one or more other elements of the final composite image, or the like. The composite image is presented to a subject or subjects 306, and one or more metrics indicative of the subject's or subjects' attentiveness to a location or locations in the composite image are recorded 310. More than one composite image may be presented in a sequence to the subject or subjects. In such an example, the selection of element images to be included in the sequence of composite images as well as the placement parameters of the element images in each image in the sequence may be selected manually or automatically. Automatic selection may be random or stochastic. These metrics of subject attentiveness are correlated with the placement parameter or parameters to characterize a level of subject interest in the selected element 312.

Figure 4:
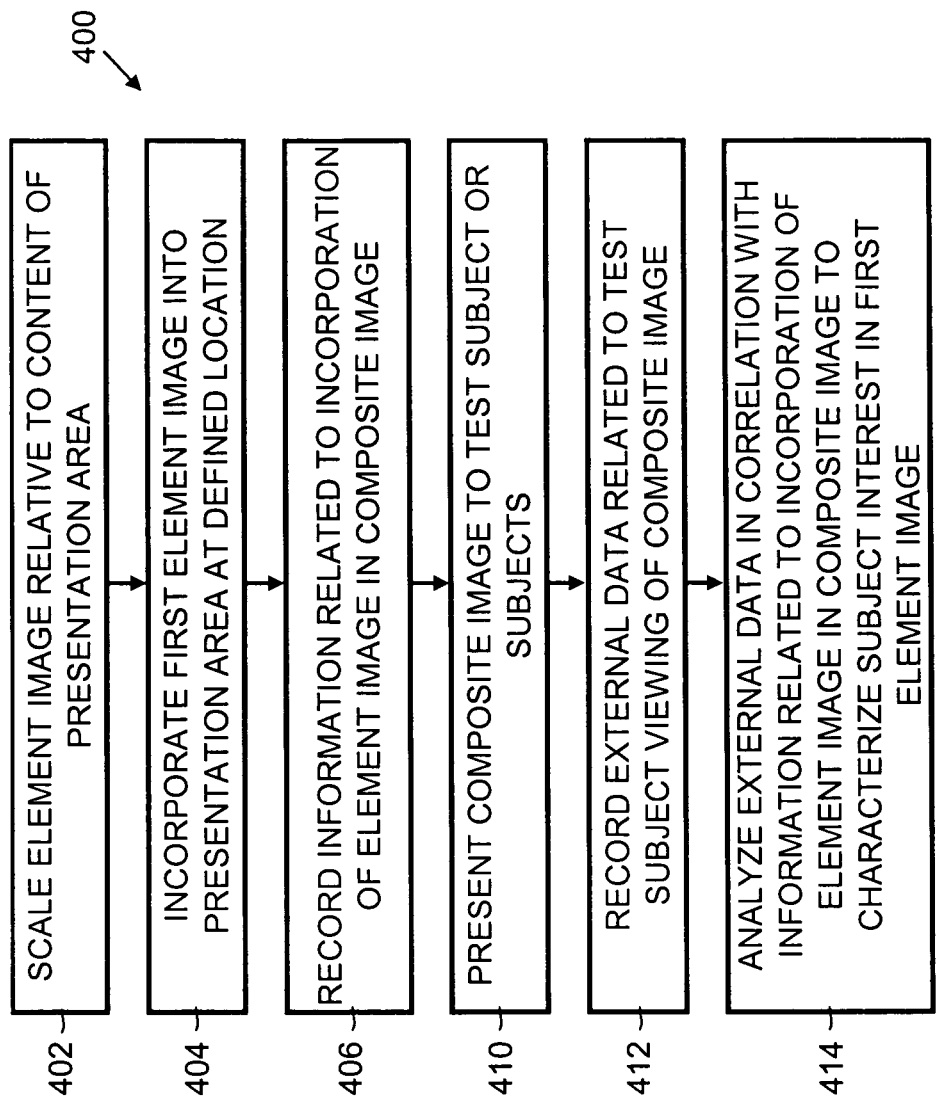
FIG. 4 is a flow chart diagram illustrating a second example of a method of implementing the disclosed subject matter.

Another implementation of the disclosed subject matter is illustrated by the method flow diagram 400 shown in FIG. 4. In this example, an element image is scaled relative to the content of a presentation area 402. The element image may optionally be selected from a predefined library. If the element image is selected from a library, the selection may be based on user input, or it may be stochastically generated as described above. The scaling may be done using one of the above-described techniques, and may include additional processing to preserve resolution and image quality. The first element image is incorporated into the presentation area at a defined location 404, which may be stochastically generated or based on user input. Information related to the incorporation of the element image is recorded 406. The recorded information may be one or more of the element image location in the composite image, the element image size, coloration, transparency or lack thereof, foreground or background placement, location relative to other elements in the composite image, and the like. Optionally, additional element images may be added to the composite image in addition to the first element image.

Once the composite image is completed, the composite image is presented to one or more test subjects 410 and external data related to the observation of the composite image by the test subject or subjects are recorded 412. These external data may be one or more measures as discussed above. The external data are analyzed in correlation with the recorded information related to the incorporation of the element image in the composite image. In this manner, one or more composite images generated in a sequence may be, for example, used in a research study to determine test subject reactions to various placements of an element image in a composite image or to test the attractiveness of on element image relative to another at similar placement in a composite image. In the example of a sequence of composite images being shown to multiple subjects, not all composite images may include all element images, and not all subjects may see all of the composite images in the sequence.

Various implementations of the subject matter described herein may be realized in digital electronic circuitry, integrated circuitry, specially designed application specific integrated circuits (ASICs), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) may include machine instructions for a programmable processor, and may be implemented in a high-level procedural and/or object-oriented programming language, and/or in assembly/machine language. The programs may be packaged, sold, or otherwise provided to users via a network or as part of a machine-readable medium such as for example any computer program product, apparatus and/or device, including but not limited to magnetic discs, optical disks, random access or read only memory, flash memory, programmable logic devices (PLDs). Such machine readable media may be used to provide machine instructions and/or data to a programmable processor, including a machine-readable medium that receives machine instructions as a machine-able readable signal. The term machine-readable signal refers to any signal used to provide machine instructions and/or data to a programmable processor.

To provide for interaction with a user, the subject matter described herein may be implemented on a computer having a display device, such as for example a cathode ray tube (CRT) or liquid crystal display (LCD) monitor, for displaying information to the user and a keyboard and a pointing device, such as for example a mouse or a trackball, by which the user may provide input to the computer. Other kinds of devices may be used to provide for interaction with a user as well. For example, feedback provided to the user may be any form of sensory feedback, such as for example visual feedback, auditory feedback, or tactile feedback. Input from the user may be received in any form, including but not limited to acoustic, speech, or tactile input.

The subject matter described herein may be implemented in a computing system that includes a back-end component, such as for example a data server, or that includes a middleware component, such as for example an application server, or that includes a front-end component, such as for example a client computer having a graphical user interface or a Web browser through which a user may interact with an implementation of the subject matter described herein, or any combination of such back-end, middleware, or front-end components. The components of such a system may be interconnected by any form or medium of digital data communication, such as for example a communication network. Examples of communication networks include a local area network (LAN), a wide area network (WAN), and the Internet. The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:

1. A computer-implemented method comprising:
generating a composite image that includes an element image, the element image being selected from a library, the composite image comprising a composite image resolution and first physical dimensions representative of a presentation area physical dimensions of a defined physical presentation area depicted in the composite image, the library comprising a plurality of element images and also comprising one or more second physical dimensions representative of object physical dimensions of at least one object shown in the element image, the generating of the composite image comprising rescaling the element image based at least in part on the first physical dimensions and the second physical dimensions to size the element image according to a scaling dimension of the element image relative to the presentation area such that the at least one object shown in the element image is included in the composite image with its object physical dimensions adjusted to a same scale as the presentation area physical dimensions;
tracking placement parameters related to inclusion of the element image in the composite image, the placement parameters comprising a location within the composite image and the scaling dimension;
presenting the composite image to a subject, the presenting occurring via a display device;
recording a metric indicative of subject attentiveness to one or more locations in the composite image; and
correlating the recorded metric indicative of subject attentiveness with the placement parameters comprising the location within the composite image and the scaling dimension to characterize a level of subject interest in the element image;
wherein one or more of the generating, the tracking, the presenting, the recording, and the correlating are performed by a system comprising at least one processor.

2. A computer-implemented method as in claim 1, further comprising stochastically generating the placement parameters.

3. A computer-implemented method as in claim 1, further comprising stochastically selecting the element image from all of the element images in the library.

4. A computer-implemented method as in claim 1, wherein the element image is selected automatically and stochastically from a user-defined subset of element images in the library.

5. A computer-implemented method as in claim 1, further comprising defining the library with one or more selected element images.

6. A computer-implemented method as in claim 1, wherein the library is a set of element images selected from a larger collection of images.

7. A computer-implemented method as in claim 1, further comprising defining a plurality of regions within the composite image such that the element image may be placed into one of the plurality of regions.

8. A computer-implemented method as in claim 1, wherein the placement parameters further comprise one or more of an orientation of the element image, a metric of a degree to which the element image is occluded by one or more features of the composite image, and a metric of transparency of the element image or a part thereof.

9. A computer-implemented method as in claim 1, wherein the metric of subject attentiveness comprises one or more of eye tracking data, input from a user input device, and input from one or more psycho-physiological measuring devices.

10. A computer-implemented method as in claim 1, further comprising:
selecting an additional element image from the library; and
including the additional element image in the composite image.

11. A computer-implemented method as in claim 1, wherein the metric indicative of the subject attentiveness comprises eye tracking data including pupil movements and dilation, eyelid separation, gaze direction when blinks occur, blink duration and frequency, divergence of right and left eye gaze directions, and saccade of the gaze.

12. A computer-implemented method as in claim 1, wherein a level of the transparency of the element image is set using alpha blending technique.

13. A computer-implemented method comprising:
scaling a first element image selected from a library relative to a content of a defined physical presentation area according to a scaling dimension, the presentation area being depicted in a composite image and having presentation area physical dimensions represented by first physical dimensions, the library comprising a plurality of element images and also comprising one or more second physical dimensions representative of object physical dimensions of at least one object shown in the element image, the scaling dimension being based on the first physical dimensions and the second physical dimensions such that the at least one object shown in the element image is included in the composite image with its object physical dimensions adjusted to a same scale as the presentation area physical dimensions;
incorporating the first element image into the presentation area at a defined location to form a composite image;
recording information related to the incorporation of the first element image into the composite image, the information related to the incorporation of the element image into the composite image comprising the scaling dimension;
presenting the composite image to one or more test subjects, the presenting occurring via a display device;
recording external data related to the test subject viewing of the composite image; and
analyzing the external data in correlation with the information related to incorporation of the element image in the composite image to characterize a level of subject interest in the element image;
wherein one or more of the scaling, the tracking, the incorporating, the recording information, the presenting, the recording external data, and the analyzing are performed by at least one processor.

14. A computer-implemented method as in claim 13, wherein the defined location is determined stochastically.

15. A computer-implemented method as in claim 13, wherein the information related to incorporation of the element image into the composite image further comprises one or more of a location of the element image within the composite image, an orientation of the element image within the composite image, and a staging of the element image within the composite image.

16. A computer-implemented method as in claim 13, wherein the external data are eye tracking data or input from a user input device related to one or more locations within the composite image.

17. A computer-implemented method as in claim 13, wherein the analysis comprises recording a number of times the one or more test subjects focus attention within an area occupied by the element image in the composite image.

18. A computer-implemented method as in claim 13, wherein the analysis comprises recording a number of times attention of the one or more test subjects transfers into or out of an area occupied by the element image in the composite image.

19. A computer-implemented method as in claim 13, wherein:
the analysis comprises determining a sequence in which attention of the one or more subjects transitions between an area occupied by the element image in the composite image and another area within the composite image; and
the analysis further comprises determining a second sequence in which attention of the one or more subjects transitions from one area within the composite image to another area within the composite image.

20. A computer-implemented method as in claim 13, further comprising recording second external data at a time corresponding to an instance in which the external data intersect an area occupied by the element image in the composite image.

21. A computer-implemented method as in claim 20, wherein the second external data are produced from one or more sources selected from computer input devices and psycho-physiological measuring devices.

22. A computer-implemented method as in claim 13, further comprising recording second external data at a time corresponding to an instance in which the external data transfer into or out of an area occupied by the element image in the composite image.

23. A computer-implemented method as in claim 22, wherein the second external data are produced from one or more sources selected from computer input devices and psycho-physiological measuring devices.

24. A computer-implemented method as in claim 13, further comprising recording second external data at a time corresponding to an instance in which the external data transition between an area occupied by the element image in the composite image and another area within the composite image.

25. A computer-implemented method as in claim 24, wherein the second external data are produced from one or more sources selected from computer input devices and psycho-physiological measuring devices.

26. A computer-implemented method comprising:
presenting a plurality of composite images to a plurality of subjects, each composite image being generated by incorporating one or more of a plurality of element images selected from a library into a presentation area according to placement parameters, the placement parameters for each of the plurality of composite images comprising a location and a scaling factor of each of the one or more of the plurality of element images within the composite image, the scaling factor for each of the one or more of the plurality of element images being determined according to first physical dimensions representative of a presentation area physical dimensions of a defined physical presentation area of the composite image and second physical dimensions representative of object physical dimensions of at least one object shown in each element image, the scaling factor causing the at least one object shown in the element image to be included in the composite image with its object physical dimensions adjusted to a same scale as the presentation area physical dimensions;
recording a metric indicative of attentiveness of each of the plurality of subjects to one or more locations in each of the plurality of composite images; and
correlating the recorded metric indicative of attentiveness of each of the plurality of subjects with the placement parameters for each element image in each of the plurality of composite images to characterize a relative level of subject interest in each of the one or more of the plurality of element images;
wherein one or more of the presenting, the recording, and the correlating are performed by at least one processor.

27. A computer-implemented method as in claim 26, wherein the one or more element images incorporated into each composite image in the plurality of composite images is selected stochastically from the library.

28. A computer-implemented method as in claim 26, further comprising stochastically generating the placement parameters for each of the one or more element images in each of the plurality of composite image.

29. A computer-implemented method as in claim 26, further comprising stochastically generating a different ordering in which the plurality of composite images is shown to one or more of the plurality of subjects.

30. A computer-implemented method as in claim 26, further comprising aggregating the metric indicative of subject attentiveness into a data set and analyzing the aggregated data set by one or more statistical measures.

\* \* \* \* \*